United States Patent
Krahbichler et al.

Patent Number: 5,957,130
Date of Patent: Sep. 28, 1999

[54] DEVICE FOR COMPENSATING FOR FLOW RESISTANCE IN A VENTILATOR/RESPIRATOR

[75] Inventors: Erik Krahbichler, Solna; Fredrik Jalde, Stockholm, both of Sweden

[73] Assignee: Siemens Elema AB, Solna, Sweden

[21] Appl. No.: 08/917,184

[22] Filed: Aug. 25, 1997

[30] Foreign Application Priority Data

Sep. 6, 1996 [SE] Sweden ................... 9603249

[51] Int. Cl.$^6$ .................................................. A62B 7/00
[52] U.S. Cl. ................... 128/205.14; 128/205.19
[58] Field of Search ............... 128/204.18, 204.21, 128/204.23, 205.14, 205.19

[56] References Cited

U.S. PATENT DOCUMENTS

| | | | |
|---|---|---|---|
| 3,339,545 | 9/1967 | Burchell | 128/205.14 |
| 3,515,134 | 6/1970 | Taylor | 128/205.14 |
| 3,905,362 | 9/1975 | Eyrick et al. | 128/205.19 |
| 4,020,834 | 5/1977 | Bird | 128/205.14 |
| 4,197,843 | 4/1980 | Bird | 128/205.14 |
| 5,065,746 | 11/1991 | Steen | 128/205.24 |
| 5,299,579 | 4/1994 | Gedeon et al. | 128/205.14 |
| 5,400,728 | 3/1995 | Jonson et al. | 128/205.19 |
| 5,507,282 | 4/1996 | Younes | 128/204.21 |
| 5,509,406 | 4/1996 | Kock et al. | 128/203.12 |
| 5,678,540 | 10/1997 | Kock et al. | 128/205.14 |

OTHER PUBLICATIONS

"Automatic Compensation of Endotracheal Tube Resistance in Spontaneously Breathing Patients," Fabry et al., Technology & Health Care, vol. 1, 1994, pp. 281–291.

*Primary Examiner*—Aaron J. Lewis
*Attorney, Agent, or Firm*—Hill & Simpson

[57] ABSTRACT

A device for compensating for flow resistance in an expiratory section of a ventilator system has a bellows system whose increase in volume during expiration is regulated by a regulatory device and a control unit, so that expired gas fills the bellows system. The increase in volume is regulated according to values measured for pressure so virtually complete compensation for flow resistance is attained. Pressure is measured with a first pressure gauge located by the bellows system, and a second pressure gauge located by the patient. The device can be a separate apparatus which is connectable to a ventilator, or can be totally integrated into the ventilator.

9 Claims, 1 Drawing Sheet

DEVICE FOR COMPENSATING FOR FLOW RESISTANCE IN A VENTILATOR/RESPIRATOR

BACKGROUND OF THE INVENTION

1. Field of the Invention

The present invention is directed to a device for compensating for flow resistance in a ventilator/respirator, and to a ventilator/respirator containing such a device.

2. Description of the Prior Art

As used herein, the term "ventilator/respirator" also refers to other equipment for providing respiratory support, such as anesthetic machines etc.

When a patient is connected to a ventilator/respirator, a series of resistances to flow, in the form of gas lines, an endotracheal tube, dehumidifier, flowmeter, bacterial filters etc., are introduced. They jointly make it harder for the patient to breathe, in particular to exhale. This is unpleasant to the patient.

A system, primarily for compensating for the resistance to flow in the endotracheal tube, is described in the article "Automatic compensation of endotracheal tube resistance in spontaneously breathing patients" by Fabry et al., Technology and Health Care, 1 (1994) 281–291, but the corresponding principle can also be applied to the entire expiratory section.

A fan is used to generate a constant negative pressure on the outlet side of the expiratory section, i.e. downstream from the expiratory section as viewed from the patient. An expiratory valve can be regulated by a valve system, exposing the expiratory channel to a larger or smaller part of this constant negative pressure. Pressure is measured in the expiratory channel at the expiratory valve and by the patient. If known, previously measured and calibrated endotracheal tubes are used, and pressure in the patient's lungs can be calculated from the flow measured near the patient. The valve system is regulated so a programed reference value for lung pressure is maintained. If the calculated value for lung pressure is too high, the valve system is caused to increase negative pressure, and vice-versa.

This known compensation system takes into account the circumstance that flow resistance is also related to flow rate. A disadvantage of this system is a risk of excessive amounts of gas being evacuated from the patient's lungs, which would therefore collapse. This is a grave threat to the patient, so compensation systems of various kinds have seldom been used in practice.

Another shortcoming is that the system does not work with "unknown" endotracheal tubes, i.e. endotracheal tubes whose flow resistance and pressure drop properties have not been specifically determined.

SUMMARY OF THE INVENTION

An object of the present invention is to provide a device which safely and effectively compensates for flow resistance in the expiratory section and which solves the aforementioned problems.

Another object of the present invention is to provide a ventilator/respirator which safely and effectively compensates for flow resistance in the expiratory section and which solves the aforementioned problems.

The above objects are achieved in accordance with the principles of the present invention in a device for compensating for flow resistance in the expiratory section of a breathing assist system, and in a breathing assist system embodying such a device, wherein the device has a negative pressure generating system which generates a negative pressure relative to pressure in the lungs of a patient, a measuring unit for determining the pressure in the patient's lungs, and a control unit which controls the negative pressure generating system, the negative pressure generating system being a bellows system connected between a first valve and a second valve, with the control unit regulating, during expiratory phases, the negative pressure generating system dependent on the pressure in the patient's lungs so that the bellows system receives expired gas via the first valve so as to generate a target negative pressure in relation to the pressure in the patient's lungs.

When a bellows system is used for generating the negative pressure, the volume the patient is able to expire can be limited. Tidal volume is appropriately the selected volume. The volume can also be selected so the patient is able to sigh and cough without difficulty.

In the present invention, the term "bellows system" refers to any volume-limiting system in which the enclosed volume can be actively regulated, in particular systems whose increase in volume can be actively regulated. Even a piston system thus can be employed in principle.

When the ventilator/respirator is equipped with a built-in device according to the above, the same advantages and safety are achieved.

DESCRIPTION OF THE PREFERRED EMBODIMENTS

Figure 1:
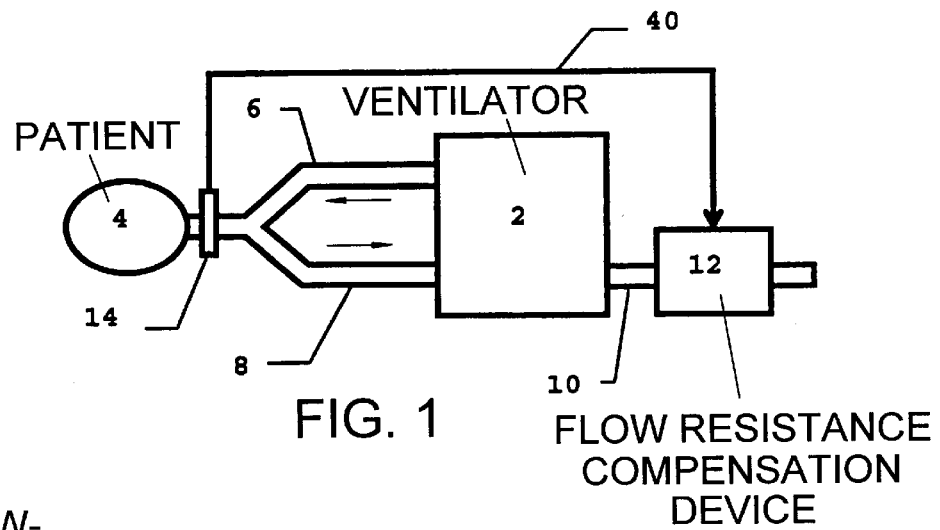
FIG. 1 shows a flow resistance compensating device in accordance with the invention connected to a ventilator.

A breathing assist device 2, such as a ventilator, is shown in FIG. 1 connected to a patient 4 so as to deliver, via an inspiratory line 6, a breathing gas to the patient 4 and, via an expiratory line 8, to evacuate breathing gas from the patient 4. The evacuated breathing gas is discharged from the ventilator 2 through an evacuation line 10.

Figure 2:
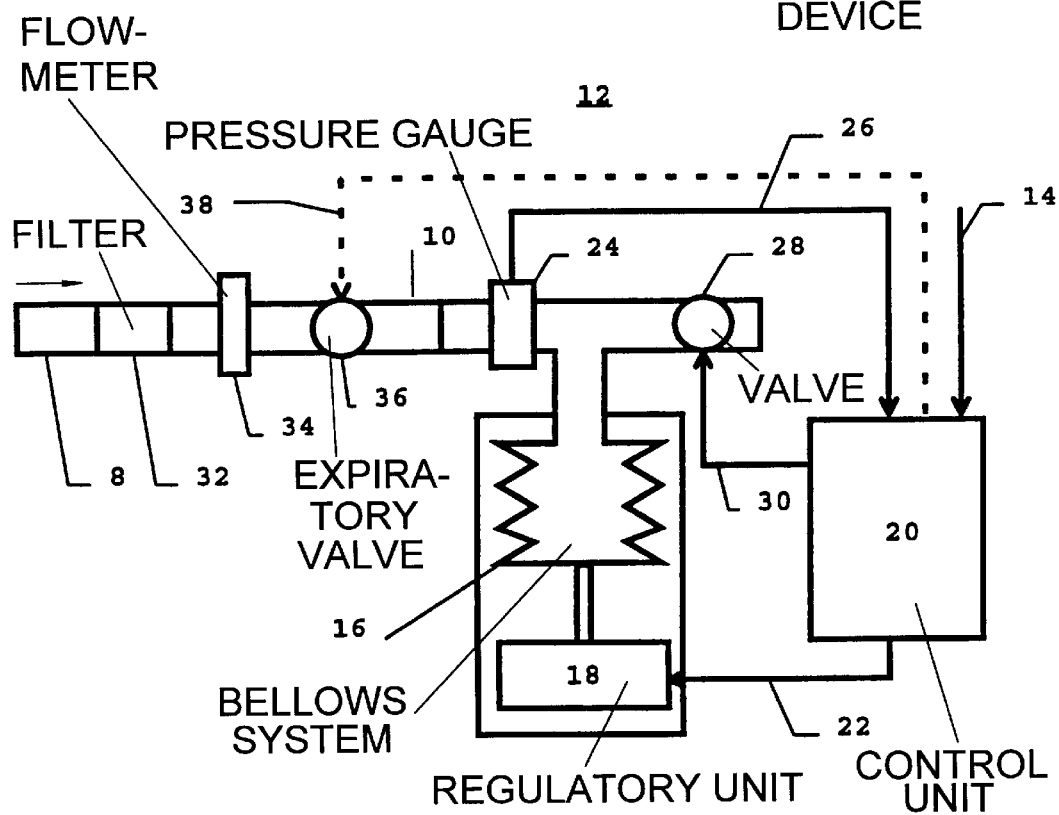
FIG. 2 shows an exemplary embodiment of a flow resistance compensating device according to the invention.

A device 12 is connected to the evacuation line 10 to compensate for flow resistance which is present in the entire expiratory part of the ventilator system, i.e. the entire flow path from the lungs of the patient 4 to the evacuation line 10. Different components, serving as inherent flow restrictors, can be arranged in this flow path (see FIG. 2), e.g. a filter 32, dehumidifier, flowmeter 34, valves 36 etc. These components also create resistance to flow.

The resistance to flow depends on the flow rate and can also vary due to occlusion of filters, etc.

The device 12 is devised to compensate actively for flow resistance and, accordingly, facilitate exhalation by the patient 4. This design is illustrated more clearly in FIG. 2 which shows that the device 12 contains a bellows 16 whose position is actively regulated by a regulatory unit 18. The regulation is preferably mechanical. The regulatory unit 18 receives control signals from a control unit 20 via a first control line 22.

A signal corresponding to pressure in the patient's lungs can be used to control the bellows system 16 so that pressure in the patient's lungs during exhalation corresponds to a reference pressure, preferably PEEP. If the fall in pressure is achieved rapidly in the initial stage of exhalation and is then maintained throughout exhalation, the patient 4 will not feel a resistance to exhalation. Pressure in the patient's lungs can be achieved in the manner described below.

Even if this control principle is sufficient for achieving the objective of the invention with good safety for the patient 4, other control principles can be utilized in achieving the same effect.

Thus, the device 12 has a first pressure gauge 24 which measures pressure in the extension of the expiratory line 8 and supplies the pressure value to the control unit 20 via a first pressure signal line 26. In a corresponding manner, a second pressure gauge 14 is arranged to measure pressure in the patient's lungs next to (at) the patient 4 (see FIG. 1) and to supply the measured pressure to the control unit 20 via a second pressure signal line 40. The second pressure gauge 14 can be located in a Y-piece connected to an endotracheal tube or can be designed for insertion into the airways of the patient 4. If a special endotracheal tube is used, with separate gas lines for inspiration and expiration, pressure in the patient's lungs can be obtained from pressure gauges inside the ventilator 2. Even if the exact pressure deep in the lungs is the target pressure, pressure in the Y-piece or the like (with or without compensation for flow) can be allowed to correspond to pressure in the patient's lungs.

The device 12 further has a first valve 28 which is controlled by the control unit 20 via second control line 30.

In the illustrated embodiment, the device 12 is connected to the evacuation line 10 on the ventilator 2. The ventilator 2 has an expiratory valve 36 which can be controlled, directly or indirectly, by the control unit 20, as shown with a dashed third control line 38.

The device 12 operates as follows. When expiration commences, the expiratory valve 36 opens fully, and the first valve 28 is kept closed. The control unit 20 is supplied with the measured pressure valves and, on the basis thereof, determines the magnitude of resistance to flow and sends a control signal to the regulatory unit 18 which accordingly acts on the bellows system 16, causing the volume of the bellows system 16 to increase. The speed at which the volume increases can be regulated so the compensation achieved by increasing the volume of the bellows system 16 matches the prevailing flow resistance as closely as possible.

When expiration has ended, the expiratory valve 36 closes, and the first valve 28 opens to discharge gas collected in the bellows system 16. Instead of being discharged directly into ambient air, collected gas can be sent to a gas analyzer (not shown) for analysis. Alternatively, an analyzer can be arranged in or by the bellows system 16, and the gas can be analyzed during expiration.

If the device 12 is incorporated into the ventilator 2, the first valve 28 can serve as an expiratory valve, and the expiratory valve 36 can be replaced with a check valve. Pressure in the bellows system should then be higher than the peak inspiratory pressure (PIP) to keep gas from leaking out of the system during the inspiratory phase. This can be regulated by means of the first valve 28 and the regulatory unit 18.

The volume of the bellows system 16 can be set so that a sufficient amount of gas always remains in the patient's lungs. In this manner, there is virtually no risk involved in using the device to compensate for flow resistance, accelerate expiration and evacuate inspired gas from the lungs, and no risk of lung collapse.

The degree of filling of the bellows system 16 can also be ascertained, i.e. the volume of expired gas. This volume can be related to the duration of expiration, and an average expiratory flow can be determined. The flowmeter 34 can then be replaced by the bellows system 16 and a timer.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for compensating for flow resistance in an expiratory section of a breathing assist device, comprising:
   means for determining a pressure in a patient's lungs and for generating an output signal indicative of said pressure;
   a negative pressure generating system which generates a negative pressure relative to said pressure in a patient's lungs, said negative pressure generating system comprising a bellows system connected between a first valve and a second valve; and
   control means for controlling said negative pressure generating system for regulating said bellows system during expiratory phases and responsive to said output signal of said means for determining a pressure in a patient's lungs for causing said bellows system to receive expired gas via said first valve for generating a target negative pressure relative to said pressure in a patient's lungs.

2. A device as claimed in claim 1 wherein said control means comprises means for discharging, during inspiratory phases, collected gas into ambient air via said second valve.

3. A device as claimed in claim 1 further comprising a pressure gauge disposed adjacent said negative pressure generating system for measuring a pressure of said expired gas, and wherein said control means comprises means for regulating said negative pressure generating system during said expiratory phases dependent on said pressure in a patient's lungs and a pressure measured adjacent said negative pressure generating system by said pressure gauge.

4. A device as claimed in claim 1 wherein said control means comprises means for regulating a speed at which a volume enclosed by said bellows system increases in generating said negative pressure.

5. A device as claimed in claim 1 wherein said first valve comprises a check valve.

6. A device as claimed in claim 1 wherein said means for determining a pressure in a patients lungs comprises a pressure gauge.

7. A device as claimed in claim 6 wherein said pressure gauge comprises a pressure gauge adapted for insertion into lower airways of a patient.

8. A device as claimed in claim 1 wherein said expiratory system of said breathing assist system has a gas outlet, and wherein said device further comprises means for connecting said device to said gas outlet.

9. A breathing assist system comprising:
   an expiratory section having an expiratory valve;
   means, connected in said expiratory system upstream from said expiratory valve, for compensating for flow resistance in said expiratory system; and
   said means for compensating for flow resistance comprising means for determining a pressure in a patient's lungs and for generating an output signal indicative of said pressure;
   a negative pressure generating system which generates a negative pressure relative to said pressure in a patient's lungs, said negative pressure generating system comprising a bellows system connected between a first valve and a second valve; and control means for controlling said negative pressure generating system for regulating said bellows system during expiratory phases and responsive to said output signal of said means for determining a pressure in a patient's lungs for causing said bellows system to receive expired gas via said first valve for generating a target negative pressure relative to said pressure in a patient's lungs.

* * * * *